(12) United States Patent
Cope et al.

(10) Patent No.: US 11,266,817 B2
(45) Date of Patent: Mar. 8, 2022

(54) CAVITATION CATHETER

(71) Applicant: Medtronic Vascular, Inc., Santa Rosa, CA (US)

(72) Inventors: Jonathan Ashley Cope, Santa Rosa, CA (US); Risa Tom Egerter, Galway (IE); Gerry Oliver McCaffrey, Tuam (IE); Peter Glynn, Galway (IE); Jack Wallis, Galway (IE); Aran Murray, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 130 days.

(21) Appl. No.: 16/661,517

(22) Filed: Oct. 23, 2019

(65) Prior Publication Data
US 2020/0129742 A1 Apr. 30, 2020

Related U.S. Application Data

(60) Provisional application No. 62/750,456, filed on Oct. 25, 2018.

(51) Int. Cl.
*A61M 25/10* (2013.01)
*A61B 17/22* (2006.01)
*A61M 25/00* (2006.01)

(52) U.S. Cl.
CPC ..... *A61M 25/104* (2013.01); *A61B 17/22012* (2013.01); *A61B 17/22022* (2013.01);
(Continued)

(58) Field of Classification Search
CPC ................ A61M 25/10; A61M 25/104; A61M 2025/1072; A61M 2025/1059; A61B 2018/00214
(Continued)

(56) References Cited

U.S. PATENT DOCUMENTS 4,445,892 A 5/1984 Hussein et al.
5,505,700 A 4/1996 Leone et al.
(Continued)

FOREIGN PATENT DOCUMENTS

CN 2614695 Y 5/2004
CN 101505822 A 8/2009
(Continued)

OTHER PUBLICATIONS

Extended European Search Report from European Counterpart Application No. 19205270.2, dated Mar. 19, 2020, 5 pp.
(Continued)

*Primary Examiner* — Melanie R Tyson
*Assistant Examiner* — Serenity A Miller
(74) *Attorney, Agent, or Firm* — Shumaker & Sieffert, P.A.

(57) ABSTRACT

In some examples, a catheter includes an elongated member including at least one balloon connected to the elongated member, the at least one balloon being configured to inflate to an expanded state. In the expanded state, the at least one balloon forms at least a portion of a cavity with a wall of a vessel of the patient. The catheter including at least one electrode carried by the elongated member and having at least one surface exposed to the cavity formed by the at least one balloon. The electrode is configured to connect to an energy source that is configured to deliver, via the electrode, an electrical signal to a fluid contained in the cavity and in contact with the electrode to cause the fluid to undergo cavitation to generate a pressure pulse wave within the fluid.

12 Claims, 13 Drawing Sheets

(52) U.S. Cl.
CPC ............... *A61B 2017/22001* (2013.01); *A61B 2017/22007* (2013.01); *A61B 2017/22011* (2013.01); *A61B 2017/22025* (2013.01); *A61M 2025/0024* (2013.01); *A61M 2025/1004* (2013.01); *A61M 2025/1052* (2013.01); *A61M 2025/1063* (2013.01)

(58) Field of Classification Search
USPC ........................................................ 606/128
See application file for complete search history.

(56) References Cited

U.S. PATENT DOCUMENTS

| | | | |
|---|---|---|---|
| 5,779,698 | A | 7/1998 | Clayman et al. |
| 6,527,759 | B1 | 3/2003 | Tachibana et al. |
| 8,568,399 | B2 | 10/2013 | Azamian et al. |
| 8,574,247 | B2 | 11/2013 | Adams et al. |
| 8,709,075 | B2 | 4/2014 | Adams et al. |
| 8,728,091 | B2 | 5/2014 | Hakala et al. |
| 8,747,416 | B2 | 6/2014 | Hakala et al. |
| 8,858,585 | B2 | 10/2014 | Stengel |
| 8,888,788 | B2 | 11/2014 | Hakala et al. |
| 8,956,352 | B2 | 2/2015 | Mauch et al. |
| 8,956,371 | B2 | 2/2015 | Hawkins et al. |
| 8,956,374 | B2 | 2/2015 | Hawkins et al. |
| 9,011,463 | B2 | 4/2015 | Adams et al. |
| 9,044,618 | B2 | 6/2015 | Hawkins et al. |
| 9,072,534 | B2 | 7/2015 | Adams et al. |
| 9,220,521 | B2 | 12/2015 | Hawkins et al. |
| 9,642,673 | B2 | 5/2017 | Adams et al. |
| 9,707,036 | B2 | 7/2017 | Anderson et al. |
| 9,730,715 | B2 | 8/2017 | Adams |
| 2007/0088246 | A1 | 4/2007 | Steward et al. |
| 2009/0312768 | A1 | 12/2009 | Hawkins et al. |
| 2010/0023088 | A1 | 1/2010 | Stack et al. |
| 2010/0114020 | A1 | 5/2010 | Hawkins et al. |
| 2010/0114065 | A1 | 5/2010 | Hawkins et al. |
| 2012/0116289 | A1 | 5/2012 | Hawkins et al. |
| 2012/0221013 | A1 | 8/2012 | Hawkins et al. |
| 2013/0030447 | A1 | 1/2013 | Adams |
| 2013/0116714 | A1 | 5/2013 | Adams et al. |
| 2014/0005576 | A1 | 1/2014 | Adams et al. |
| 2014/0039513 | A1 | 2/2014 | Hakala et al. |
| 2014/0046229 | A1 | 2/2014 | Hawkins et al. |
| 2014/0046353 | A1 | 2/2014 | Adams |
| 2014/0163592 | A1 | 6/2014 | Hawkins et al. |
| 2014/0288570 | A1 | 9/2014 | Adams |
| 2015/0039002 | A1 | 2/2015 | Hawkins |
| 2016/0008016 | A1 | 1/2016 | Cioanta et al. |
| 2016/0135828 | A1 | 5/2016 | Hawkins et al. |
| 2016/0184570 | A1 | 6/2016 | Grace et al. |
| 2017/0135709 | A1 | 5/2017 | Nguyen et al. |
| 2018/0153568 | A1 | 6/2018 | Kat-Kuoy |
| 2018/0264247 | A1 | 9/2018 | Mantri et al. |
| 2019/0117242 | A1 | 4/2019 | Lawinger et al. |

FOREIGN PATENT DOCUMENTS

| | | |
|---|---|---|
| CN | 104582597 A | 4/2015 |
| CN | 105536123 A | 5/2016 |
| EP | 0623360 B1 | 3/1999 |
| EP | 1100385 B1 | 1/2006 |
| EP | 2848225 A1 | 3/2015 |
| WO | 00/07508 A1 | 2/2000 |
| WO | 2016064076 A1 | 4/2016 |
| WO | 2016109736 A1 | 7/2016 |

OTHER PUBLICATIONS

Locke et al., "Electrohydraulic Discharge and Nonthermal Plasma for Water Treatment," Industrial & Engineering Chemistry Research, Dec. 31, 2005, 24 pp.

Siegel et al., "Percutaneous Ultrasonic Angioplasty: Initial Clinical Experience," The Lancet, vol. 334, No. 8666, Sep. 1989, p. 772-774.

Siegel et al., "In Vivo Ultrasound Arterial Recanalization of Atherosclerotic Total Occlusions," Journal of the American College of Cardiology, vol. 15, Issue 2, Feb. 1990, p. 345-351.

Rosenschein et al., "Ultrasound Imaging-Guided Noninvasive Ultrasound Thrombolysis: Preclinical Results," Journal of the American Heart Association, vol. 102, Issue 2, Jul. 2000, 8 pp.

CAVITATION CATHETER

This application claims the benefit of U.S. Provisional Application No. 62/750,456, which was filed on Oct. 25, 2018, and is entitled, "CAVITATION CATHETER." The entire content of U.S. Provisional Application No. 62/750,456 is incorporated herein by reference.

TECHNICAL FIELD

This disclosure relates to medical catheters.

BACKGROUND

Medical catheters have been proposed for use with various medical procedures. For example, medical catheters may be used to access and treat defects in blood vessels, such as, but not limited to, treatment of calcific atherosclerotic plaque buildup within the vasculature wall of vasculature associated with cardiovascular disease. Some techniques for treating such diseases may include balloon angioplasty alone or balloon angioplasty followed by stenting of the vasculature. However, such techniques may fail to address certain types of plaque buildup and/or result in re-stenotic events.

SUMMARY

In some aspects, the disclosure describes example medical devices, such as catheters, that include one or more occlusion balloons and at least one electrode configured to deliver energy intravascularly to fluid in contact with a vasculature wall to induce cavitation within the fluid. The cavitation may be used to treat a defect in the vasculature of the patient. For example, the cavitation may produce a high-energy pressure pulse wave that, when directed at a vasculature wall, may be used to disrupt and fracture calcific atherosclerotic plaque buildup within the vasculature wall. The disruption and fracture of the plaque may allow the vasculature to be more easily expanded to achieve better blood flow through the vessel. In some examples, the use of such devices may reduce or eliminate the need for subsequent stenting of the vasculature and reduce the chance of restenosis. In some other aspects, the disclosure describes methods of using the catheters described herein.

Clause 1: In one example, a catheter includes an elongated member configured to be navigated through vasculature of a patient to a target treatment site; a balloon connected to the elongated member, the balloon being inflatable to an expanded state to occlude a vessel of the patient; and an electrode positioned around a portion of an exterior of the balloon, the electrode configured to electrically connect to an energy source configured to deliver an electrical signal, via the electrode, to a fluid in contact with the electrode to cause the fluid to undergo cavitation to generate a pressure pulse wave within the fluid, where, when the balloon is in the expanded state, the electrode is configured to cause the balloon to form a first lobe and a second lobe by restricting the expansion of the balloon, the first lobe and the second lobe being configured to form a cavity when the first lobe and the second lobe contact a wall of the vessel in the expanded state.

Clause 2: In some of the examples of the catheter of clause 1, the electrode includes a concentric electrode including an outer electrically conductive band and an inner electrically conductive band separated by an electrically insulating layer, an aperture extending through the outer electrically conductive band and the electrically insulating layer to provide fluid communication between the outer and the inner electrically conductive bands.

Clause 3: In some of the examples of the catheter of clause 1 or 2, the electrode includes a cylindrical body, the cylindrical body configured to maintain a cylindrical shape when the balloon is inflated to the expanded state.

Clause 4: In some of the examples of the catheter of any one of clauses 1 to 3, where the electrode defines at least one surface exposed to the cavity.

Clause 5: In some of the examples of the catheter of any one of clauses 1 to 4, the balloon includes a wrapped balloon including a plurality of pleats, where, when the balloon is in a non-expanded state, the pleats are wrapped around the elongated member.

Clause 6: In some of the examples of the catheter of clause 5, the catheter includes an electrical conductor electrically coupled to the electrode, the electrical conductor extending along the elongated member and positioned along an exterior of the wrapped balloon.

Clause 7: In some of the examples of the catheter of clause 6, where, when the balloon is in the non-expanded state, at least one pleat of the plurality of pleats is folded over the electrical conductor.

Clause 8: In some of the examples of the catheter of clause 6, where, when the balloon is in the non-expanded state, the electrical conductor is positioned adjacent to an apex of at least one pleat of the plurality of pleats.

Clause 9: In some of the examples of the catheter of any one of clauses 1 to 8, the elongated member defines an inner lumen configured to receive a guidewire.

Clause 10: In some of the examples of the catheter of any one of clauses 1 to 9, the balloon defines at least one perfusion aperture configured to supply a fluid to the cavity.

Clause 11: In some of the examples of the catheter of any one of clauses 1 to 10, the balloon includes at least one of an anti-restenotic agent, an anti-proliferative agent, or an anti-inflammatory agent.

Clause 12: In some of the examples of the catheter of any one of clauses 1 to 11, the electrode includes a first electrode and the cavity includes a first cavity, the catheter further including a second electrode positioned around a distal portion of the exterior of the balloon, where, when the balloon is in the expanded state, the second electrode is configured to cause the balloon to form a third lobe and the second lobe by restricting the expansion of the balloon, the second lobe and the third lobe configured to form a second cavity containing the second electrode when the second lobe and the third lobe contact the wall of the vessel in the expanded state.

Clause 13: In one example, a catheter includes an elongated member configured to be navigated through vasculature of a patient to a target treatment site; a first balloon connected to the elongated member, the first balloon being inflatable to an expanded state to occlude a proximal portion of a vessel proximal to the target treatment site; a second balloon connected to the elongated member, the second balloon being inflatable to an expanded state to occlude a distal portion of the vessel distal to the target treatment site, and where when the first and second balloons are in the respective expanded states within the vessel, a cavity is defined between the elongated member and the target treatment site, the cavity being exterior to the first and second balloons; and an electrode including an electrically conductive band attached to the elongated member, the electrode configured to be connected to an energy source configured to deliver an electrical signal to a fluid within the cavity and in contact with the electrode to cause the fluid to undergo cavitation to generate a pressure pulse wave within the fluid.

Clause 14: In some of the examples of the catheter of clause 13, the electrode includes a concentric electrode where the electrically conductive band forms an outer electrically conductive band, the concentric electrode further including an inner electrically conductive band separated from the outer electrically conductive band by an electrically insulating layer, an aperture extending through the outer electrically conductive band and the electrically insulating layer to provide fluid communication between the inner and the outer electrically conductive bands.

Clause 15: In some of the examples of the catheter of clause 13, the electrically conductive band forms a first electrically conductive band on the elongated member, the first electrically conductive band having a first surface area exposed to the cavity, the catheter further including a second electrically conductive band on the elongated member, the second electrically conductive band having a second surface area exposed to the cavity, the first and the second electrically conductive bands configured to deliver an electrical signal between the first and the second surface areas through the fluid within the cavity to cause the fluid to undergo cavitation.

Clause 16: In some of the examples of the catheter of clause 15, the first surface area and the second surface area are separated by a distance of at least about 2 mm.

Clause 17: In some of the examples of the catheter of any one of clauses 13 to 16, the elongated member defines a lumen and at least one port connecting the lumen to the cavity and the lumen and the at least one port are configured to at least one of perfuse the cavity with the fluid or aspirate the cavity.

Clause 18: In some of the examples of the catheter of clause 17, the lumen and the at least one port are configured to perfuse the cavity with the fluid and aspirate the cavity.

Clause 19: In some of the examples of the catheter of any one of clauses 13 to 18, the elongated member the defines an inner lumen configured to receive a guidewire.

Clause 20: In some of the examples of the catheter of any one of clauses 13 to 19, where at least one of the first balloon or the second balloon includes at least one of an anti-restenotic agent, an anti-proliferative agent, or an anti-inflammatory agent.

Clause 21: In some of the examples of the catheter of any one of clauses 13 to 20, further including an electrical wire that extends along the elongated member, a surface of the electrical wire being exposed within the cavity, the electrical wire configured to be connected to the energy source configured to deliver an electrical signal between the surface of the electrical wire and the electrode.

Clause 22: In some of the examples of the catheter of clause 21, where a plurality of surfaces of the electrical wire are exposed to the fluid within the cavity, each exposed surface of the plurality of exposed surfaces forming an electrode.

Clause 23: In one example, a catheter includes an elongated member configured to be navigated through vasculature of a patient to a target treatment site; a first balloon connected to the elongated member, the first balloon being inflatable to an expanded state to occlude a proximal portion of a vessel proximal to the target treatment site; a second balloon connected to the elongated member, the second balloon being inflatable to an expanded state to occlude a distal portion of the vessel distal to the target treatment site, and where when the first and second balloons are in the respective expanded states within the vessel, a cavity is defined between the elongated member and the target treatment site, the cavity being exterior to the first and second balloons; and an electrical wire that extends along the elongated member, the electrical wire defining a plurality of exposed surfaces within the cavity, each exposed surface of the plurality of exposed surfaces forming a respective electrode, where the electrical wire is configured to be connected to an energy source configured to deliver an electrical signal to a fluid within the cavity and in contact with the plurality of exposed surfaces to cause the fluid to undergo cavitation to generate a pressure pulse wave within the fluid.

Clause 24: In some of the examples of the catheter of clause 23, the electrical wire includes a first electrical wire and the plurality of exposed surfaces include a first plurality of exposed surfaces, the catheter further including a second electrical wire that extends along the elongated member, the second electrical wire defining at least one exposed surface within the cavity forming a return electrode, where the second electrical wire is configured to be connected to the energy source configured to deliver the electrical signal between the at least one exposed surface of the second electrical wire and the plurality of exposed surfaces of the first electrical wire to cause the fluid to undergo cavitation.

Clause 25: In some of the examples of the catheter of clause 23 or 24, where adjacent exposed surfaces of the plurality of exposed surfaces are separated by a distance of at least about 2 mm.

Clause 26: In some of the examples of the catheter of any one of clauses 23 to 25, the elongated member defines a lumen and at least one port connecting the lumen to the cavity, where the lumen and the at least one port are configured to at least one of perfuse the cavity with the fluid or aspirate the cavity.

Clause 27: In some of the examples of the catheter of clause 26, the lumen and the at least one port are configured to perfuse the cavity with the fluid and aspirate the cavity.

Clause 28: In some of the examples of the catheter of any one of clauses 23 to 27, the elongated member the defines an inner lumen configured to receive a guidewire.

Clause 29: In some of the examples of the catheter of any one of clauses 23 to 28, where at least one of the first balloon or the second balloon includes at least one of an anti-restenotic agent, an anti-proliferative agent, or an anti-inflammatory agent.

Clause 30: In one example, a method includes introducing a catheter through vasculature of a patient to a target treatment site, the catheter including an elongated member including a distal portion configured to be navigated through the vasculature of the patient; a first balloon connected to the elongated member; a second balloon connected to the elongated member and distal to the first balloon; and at least one electrode carried by the elongated member between the first and second balloons. The method includes inflating the first and second balloons to an expanded state, where the first balloon occludes a proximal portion of a vessel proximal to the target treatment site and the second balloon occludes a distal portion of the vessel distal to the target treatment site, where the first and second balloons in the respective expanded states within the vessel form a cavity defined between the elongated member and the target treatment site, the cavity being exterior to the first and the second balloons; filling the cavity with a fluid; and delivering energy to the fluid within the cavity using the at least one electrode to cause the fluid to undergo cavitation and generate a pressure pulse wave within the fluid.

Clause 31: In some of the examples of the method of clause 30, inflating the first and second balloons includes inflating the first balloon prior to inflating the second balloon.

Clause 32: In some of the examples of the method of clause 30, inflating the first and second balloons includes inflating the second balloon prior to inflating the first balloon.

Clause 33: In some of the examples of the method of clause 30, inflating the first and second balloons includes simultaneously inflating the first balloon and the second balloon.

Clause 34: In some of the examples of the method of any one of clauses 30 to 33, delivering the electrical signal includes delivering a plurality of electrical pulses having a pulse width of about 1 microsecond (µs) to about 200 (µs).

Clause 35: In some of the examples of the method of any one of clauses 30 to 34, the method includes repositioning the catheter and inflating the first or the second balloon to expand the vessel after a pressure pulse wave therapy has been performed by the at least one electrode.

Clause 36: In some of the examples of the method of any one of clauses 30 to 35, the method includes aspirating the cavity formed by the first and second balloons after a pressure pulse wave therapy has been performed by the at least one electrode.

The details of one or more examples are set forth in the accompanying drawings and the description below. Other features, objects, and advantages of examples according to this disclosure will be apparent from the description and drawings, and from the claims.

DETAILED DESCRIPTION

This disclosure describes catheters, such as intravascular catheters that include a relatively flexible elongated member (e.g., the body of the catheter) configured to be navigated through vasculature of a patient to a target treatment site within the vasculature. The catheters may each include one or more occlusion balloons connected to the elongated member, the one or more balloons being configured to define a cavity between the elongated member and a wall of a vessel when the one or more balloons are in an expanded state. The catheter further includes one or more electrodes configured to deliver an electrical signal (e.g., an electrical pulse) through the fluid captured in the cavity defined between (but external to) the one or more balloons and the vessel wall. The energy transmitted to the fluid may rapidly heat the fluid to produce a short-lived gaseous steam/plasma bubble within the fluid that quickly collapses (e.g., cavitates), releasing energy in the form of a pressure pulse wave. The pulse wave may be used to treat a defect in the vasculature of the patient at the target treatment site.

In some examples, the target treatment site may be a site within the vasculature that has a defect that may be affecting blood flow through the vasculature. For example, the target treatment site may be a portion of the vasculature wall that includes a calcified lesion, e.g., calcific atherosclerotic plaque buildup. A calcified lesion can cause partial or full blockages of blood bearing vasculatures, which can result in adverse physiological effects to the patient. Such lesions may be very hard and difficult to treat using traditional methods, such as balloon angioplasty, stenting, thrombectomy, atherectomy, or other interventional procedures. The pressure pulse wave resulting from the cavitation procedure using a catheter described herein may impact the calcified lesion (or other defect at the treatment site) to fracture or disrupt at least part of the lesion. This treatment of the calcified lesion may be used in conjunction with a treatment balloon to help open-up the blood vessel of the patient, improving blood flow in the blood vessel. For example, the treatment of the calcified lesion using the catheters described herein may help restore the vasculature to a normal or at least increased flow diameter.

Figure 1:
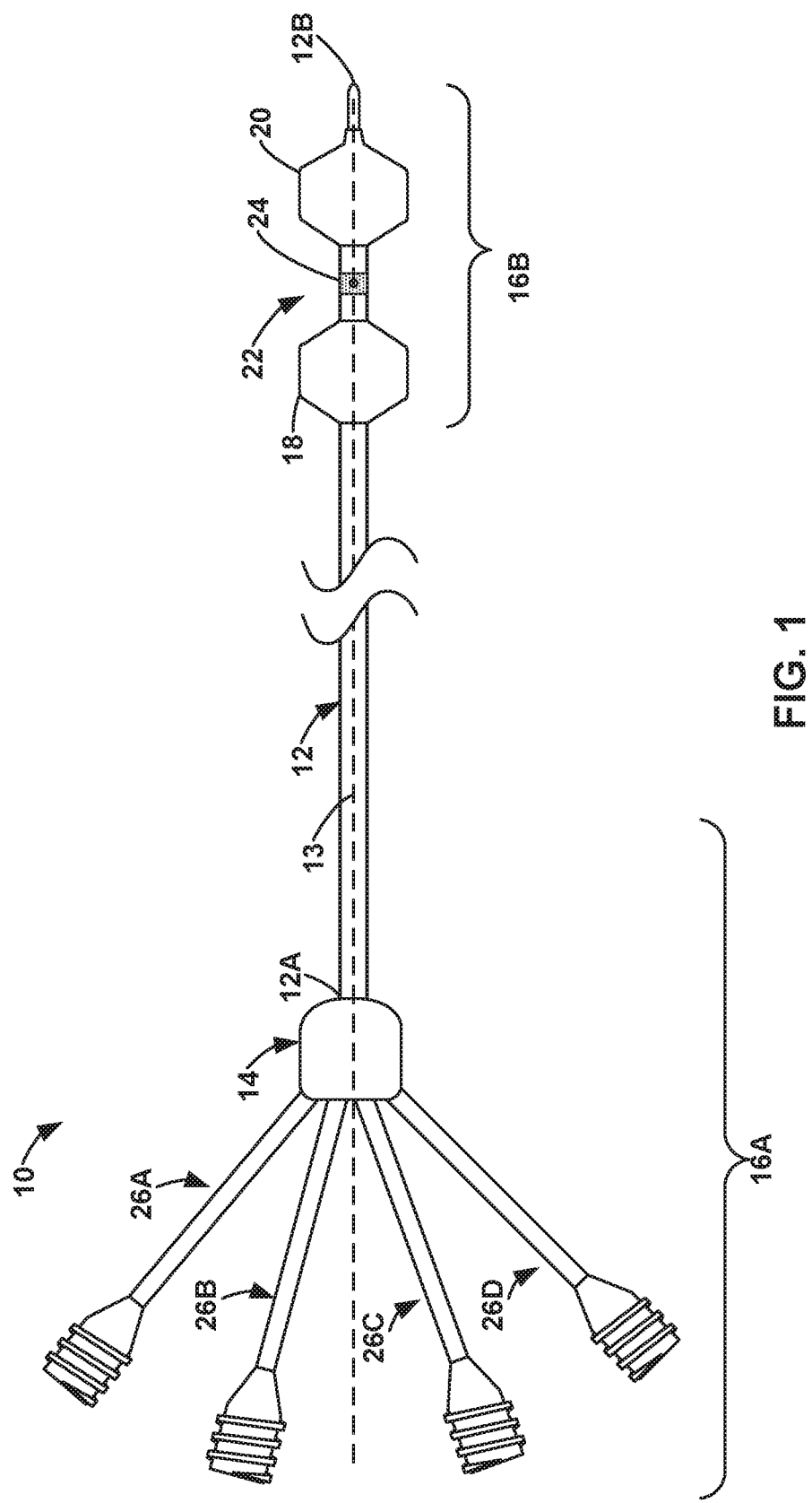
FIG. 1 is a schematic side view of an example catheter, which includes an elongated member, the side view showing the catheter along a longitudinal axis of the elongated member.

FIG. 1 is a schematic side view of an example catheter 10, which includes an elongated member 12 extending from proximal end 12A to distal end 12B. The side view of catheter 10 shown in FIG. 1 illustrates catheter 10 along a longitudinal axis 13 of elongated member 12. Catheter 10 includes a hub 14 connected to proximal end 12A of elongated member 12. Hub 14, including proximal end 12A of elongated member 12, forms part of a proximal portion 16A of catheter 10. Catheter 10 also includes a distal portion 16B that includes distal end 12B of elongated member 12. The designations of proximal and distal portion 16A and 16B are used to describe different regions of catheter 10 (as divided along a length of catheter 10) and may be of any suitable length. In some examples, elongated member 12 may also be characterized as having one or more intermediate portions separating the proximal and distal portions 16A and 16B.

Distal portion 16B of catheter 10 includes a first balloon 18 and a second balloon 20 connected to elongated member 12. First and second balloons 18 and 20 are configured to inflate to an expanded state to occlude a proximal and a distal portion of a vessel respectively to form a cavity 22 between first and second balloons 18 and 20. In some examples, cavity 22 may be a closed cavity between first and second balloons 18, 20, and a wall of a vessel of a patient (not shown in FIG. 1). Distal portion 16B also includes at least one electrode 24 carried by elongated member 12 and positioned between first and second balloons 18 and 20. For example, as describe further below, electrode 24 may be mechanically connected to elongated member 12, integrally formed with elongated member 12, or the like. Electrode 24 includes at least one surface exposed to a fluid received within cavity 22.

In some examples, catheter 10 may include a hub 14 positioned at proximal portion 16A. Proximal end 12A of elongated member 12 is received within hub 14 and can be mechanically connected to hub 14 via an adhesive, welding, or another suitable technique or combination of techniques. Hub 14 may include one or more supply tubes 26A, 26B, 26C, 26D (collectively "supply tubes 26"). Supply tubes 26 may provide access to the various components of distal portion 16B of elongated member 12 and may be used for accessing or transporting various components through elongated member 12 (e.g., a guidewire, fluids, electrical conductors, aspiration force, or the like). For example, one or more of supply tubes 26 may define a lumen that extends through elongated member 12 to one or both of first balloon 18 and second balloon 20, and a fluid may be introduced through the lumen to inflate the balloons 18, 20 to an expanded state that occludes a vessel of a patient. Additionally, or alternatively, one or more of supply tubes 26 may be used to electrically connect electrode 24 to an energy source (e.g., energy source 70 of FIG. 7); used to perfuse or aspirate cavity 22; used to introduce a guidewire into a lumen of elongated member 12; and the like.

In some examples, catheter 10 may include a strain relief body (not shown), which may be a part of hub 14 or may be separate from hub 14. The strain relief body may extend distally from hub 14 and may help reduce mechanical strain between hub 14 and elongate member 12. Additionally, or alternatively, proximal portion 16A of catheter 10 can include another structure in addition or instead of hub 14. For example, catheter hub 14 may include one or more luers or other mechanisms for establishing mechanical connections, fluidic connections, or other types of connections between catheter 10 and other devices.

In some examples, elongated member 12 of catheter 10 may be used to access relatively distal vasculature locations in a patient or other relatively distal tissue sites (e.g., relative to the vasculature access point). Example vasculature locations may include, for example, locations in a coronary artery, peripheral vasculature (e.g., carotid, iliac, or femoral artery, or a vein), cerebral vasculature, or a heart valve (e.g., aortic valve, mitral valve, tricuspid valve, or the like). In some examples, elongated member 12 is structurally configured to be relatively flexible, pushable, and relatively kink- and buckle- resistant, so that it may resist buckling when a pushing force is applied to proximal portion 16A of catheter 10 to advance elongated member 12 distally through vasculature, and so that it may resist kinking when traversing around a tight turn in the vasculature. Unwanted kinking and/or buckling of elongated member 12 may hinder a clinician's efforts to push the catheter body distally, e.g., past a turn in the vasculature.

Elongated member 12 has a suitable length for accessing a target tissue site within the patient from a vasculature access point. The length may be measured along the longitudinal axis of elongated member 12. The working length of elongated member 12 may depend on the location of the lesion within vasculature. For example, if catheter 10 is a catheter used to access a coronary, carotid, or abdominal artery, elongated member 12 may have a working length of about 50 centimeters (cm) to about 200 cm, such as about 110 cm, although other lengths may be used. In other examples, or for other applications, the working length of elongated member 12 may have different lengths.

The outer diameter of elongated member 12 may be of any suitable size or dimension including, for example, between about 1 millimeter (mm) and about 12 mm. In some examples, the outer diameter may be substantially constant (e.g., uniform outer diameter), tapered (e.g. tapered or step change to define a narrower distal portion), or combinations thereof. In some examples, elongated member 12 of catheter 10 may have a relatively small outer diameter which may make it easier to navigate through a tortuous vasculature.

In some examples, at least a portion of an outer surface of elongated member 12 may include one or more coatings, such as, but not limited to, an anti-thrombogenic coating, which may help reduce the formation of thrombi in vitro, an anti-microbial coating, and/or a lubricating coating. In some examples, the entire working length of elongated member 12 is coated with the hydrophilic coating. In other examples, only a portion of the working length of elongated member 12, e.g., including distal portion 16B, may be coated with the hydrophilic coating. This may provide a length of elongated member 12 distal to hub 14 that does not include a hydrophilic coating and with which the clinician may grip elongated member 12, e.g., to rotate elongated member 12 or push elongated member 12 through vasculature. In some examples, the entire working length of elongated member 12 or portions thereof may include a lubricious outer surface, e.g., a lubricious coating. The lubricating coating may be configured to reduce static friction and/or kinetic friction between elongated member 12 and tissue of the patient as elongated member 12 is advanced through the vasculature.

In some examples, elongated member 12 may include one or more radiopaque markers which may help a clinician determine the positioning of elongated member 12 relative to a target treatment site. For example, one or more radiopaque markers may be positioned proximal or distal to first balloon 18, proximal or distal to second balloon 20, in between first and second balloon 18 and 20, adjacent to electrode 24, or combinations thereof. In some examples, portions of electrode 24 itself may be radiopaque.

Figure 2:
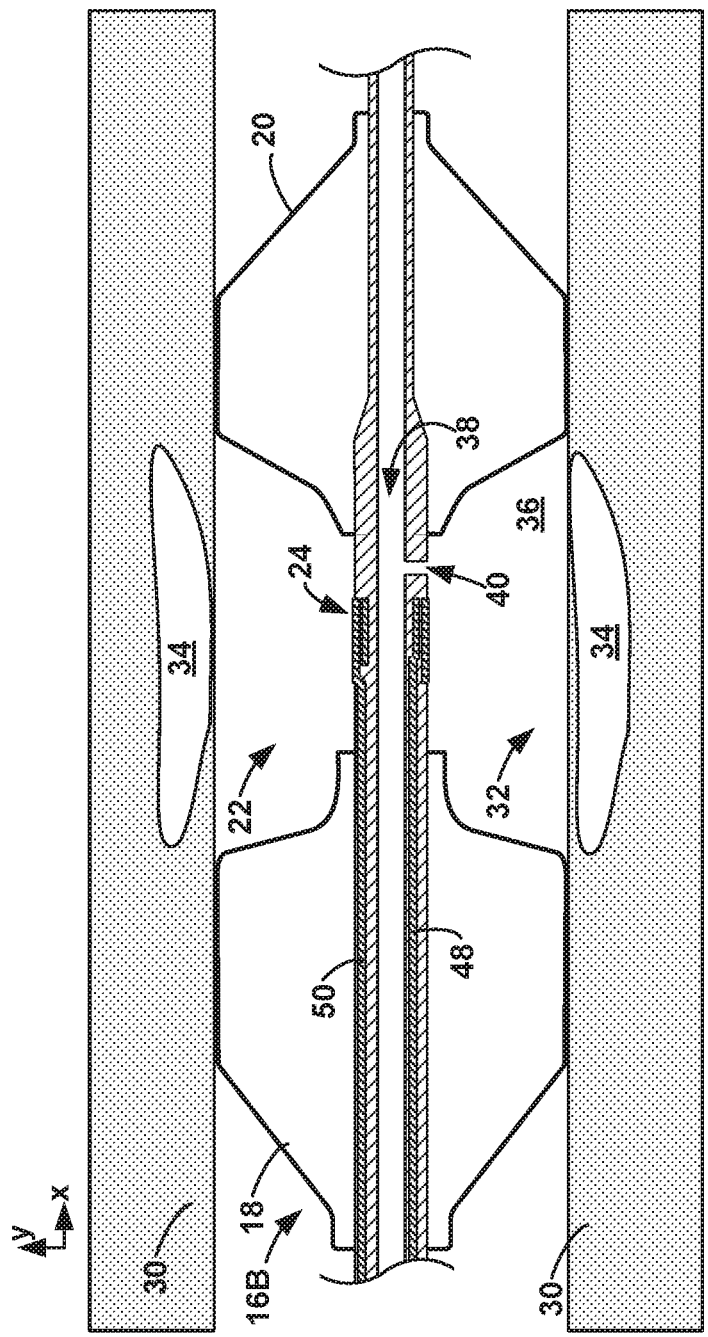
FIG. 2 is an enlarged conceptual cross-sectional view of the distal portion of the catheter of FIG. 1 taken along the longitudinal axis of the elongated member.

FIG. 2 is an enlarged conceptual cross-sectional view of distal portion 16B of catheter 10 of FIG. 1 taken along longitudinal axis 13 of elongated member 12. FIG. 2 shows distal portion 16B deployed within vessel 30 of a patient. Vessel 30 includes a target treatment site 32 containing a calcified lesion 34 on or within a wall of vessel 30. The location of lesion 34 in FIG. 2 is one example, and lesion 34 may be have another location on or within the vessel wall in other examples. In some examples, lesion 34 may be superficial or a deep calcification within the tissue of vessel 30. Additionally, or alternatively, lesion 34 may be on or within a heart valve (e.g., aortic valve).

Distal portion 16B of elongated member 12 includes first balloon 18 and second balloon 20 mechanically connected to elongated member 12. First balloon 18 is mechanically connected to elongated member 12 at a position proximal to second balloon 20. Thus, first balloon 18 may be referred to as a proximal balloon and second balloon 20 may be referred to as a distal balloon.

Balloons 18 and 20 are each configured to be expanded from a deflated stated to an expanded state via an inflation fluid delivered to the respective balloon via an inflation lumen (not shown) of elongate body 12, which may be accessed via one or more of supply tubes 26 (FIG. 1). In some examples, inflating first and second balloons 18 and 20 independently may useful to ensure each balloon is expanded properly to conform to the contours of the vessel 30. Additionally, as discussed further below, inflating first and second balloons 18 and 20 independently may allow for blood between first and second balloons 18 and 20 to be removed prior to both balloons being fully expanded. In other examples of catheter 10, first and second balloons 18 and 20 can be inflated via the same inflation lumen or separate inflation lumens.

In the respective expanded states within vessel 30, first and second balloons 18 and 20 inflate and conform to engage with the wall of vessel 30. First balloon 18 engages with vessel 30 at a position proximal to target treatment site 32 to prevent blood from flowing through vessel 30 during a cavitation procedure and second balloon 20 engages with vessel 30 at a position distal to target treatment site 32 and occludes vessel 30. In some examples, catheter 10 including at least two shorter balloons 18 and 20 may improve deliverability of catheter 10 relative to a catheter including a longer balloon (e.g., longer than the combined length of the balloons 18, 20 or longer than one of the balloons 18, 20). For example, when catheter 10 is configured for use in some procedures, such as some coronary cavitation procedures, first and second balloons 18 and 20 may be relatively short (e.g., about 3 mm to about 4 mm) compared to a single balloon extending over all of electrodes 24. The respective length of the balloons may improve deliverability and engagement with vessel 30, particularly in examples where vessel 30 is tortuous. For example, balloons 18, 20 may engage with different portions of the vessel 30 when inflated, rather than engaging with a continuous length of vessel 30. This may help reduce, for example, strain on a curved vessel 30. Further, two balloons 18, 20 may increase a flexibility of catheter 10 (compared to a catheter including a single longer balloon), thereby increasing an ease of delivery of catheter 10 through vessel 30 as well as the flex of catheter 10 when balloons 18, 20 are inflated within a curved vessel 30.

In addition, in some examples, by configuring catheter 10 such that first and second balloons 18 and 20 can inflate independently, the balloons may reduce the strain or torque on vessel 30 when inflated compared to a longer balloon, e.g., having a length equal to a combined length of balloons 18, 20. Relatively shorter balloons may help mitigate adverse effects on vessel 30 if the balloons are inflated at a bend in vessel 30.

Collectively in their expanded states, first and second balloons 18 and 20 create cavity 22 adjacent to target treatment site 32 that can be filled with a conductive fluid (e.g., blood or saline) used for the cavitation procedure. In their expanded states, first and second balloons 18 and 20 may also help center electrode 24 within vessel 30, which may help ensure a more equal distribution of the pressure pulse wave against the wall of vessel 30 during the cavitation process as well as reduce the chance of localized heating along the wall of vessel 30 by electrode 24.

First and second balloons 18 and 20 may each be formed from any suitable material, such as a flexible polymeric material that is configured to form a tight seal with elongated member 12. In some examples, first and second balloons 18 and 20 may be formed physically separate from elongated member 12 and attached to an exterior surface of elongated member 12 via co-extrusion, bonding, adhesives, or the like. In other examples, first and second balloons 18 and 20 may be integrally formed with elongated member 12 such that one or both balloons 18, 20 are embedded or at least partially embedded in elongated member 12. In some examples, first and second balloons 18 and 20 may be constructed using a flexible polymeric material including, for example, nylon 12, polyethylene, polyethylene terephthalate (PET), silicone, polyvinyl chloride, polypropylene, polyurethanes, polyamides, polyesters, latex, natural rubber, synthetic rubber, polyether block amides, or the like. Additionally, or alternatively first and second balloons 18 and 20 may be constructed with an electrically insulative material.

In some examples, first and second balloons 18 and 20 may be configured to be deflatable via a vacuum or other stable source to forcibly remove fluid from the balloon, thereby allowing for quicker collapse and/or a lower cross-sectional profile after the cavitation procedure is completed. Additionally, or alternatively, first and second balloons 18 and 20 may include one or more perfusion ports allowing fluid to continuously flow from the balloon into vessel 30.

First and second balloons 18 and 20 may have any suitable size or shape. In some examples, first and second balloons 18 and 20 may have the same size and/or shape, while in other examples first and second balloons 18 and 20 may have different sizes and/or shapes. Constructing catheter 10 to include balloons of different sizes or shape may be useful where catheter 10 is disposed within a vessel with an irregular configuration or disposed adjacent to a heart valve (e.g., aortic valve). For example, first or second balloons 18 and 20 may be sized and configured to anchor in the heart valve for use in procedures in which catheter 10 is used to treat calcified lesion in or near the heart valve. In some such examples, first and second balloons 18 and 20 may define a cross sectional diameter of about 30 mm to about 80 mm in the expanded states so that the balloons anchor on different sides of the heart valve with the valve being positioned within cavity 22. In examples in which catheter 10 is configured for use in a coronary cavitation procedure, first and second balloons 18 and 20 may define a cross sectional diameter in the expanded state equal to or greater than the cross-sectional diameter of vessel 30 (e.g., on the order of about 2 mm to about 4 mm). Additionally, or alternatively, first and second balloons 18 and 20 may exhibit a cross sectional diameters that is configured to conform to a range of vessel diameters when inflated to the expanded state.

First and second balloons 18 and 20 may also have any suitable length (measured along longitudinal axis 13) which may depend, for example, on the length of calcified lesion 34 or the size and shape of vessel 30. For some procedures used to treat calcifications in or near a heart valve (e.g., aortic valve) of a patient, first and second balloons 18 and 20 may each define a length of about 5 mm to about 30 mm with a total length (including the length of cavity 22) of about 15 mm to about 100 mm. For some procedures used to treat calcifications in or near the coronary vasculature, first and second balloons 18 and 20 may define a length of about 1 mm to about 4 mm. First and second balloons 18 and 20 may also be separated by any suitable length along longitudinal axis 13 so that the target treatment site 32 is positioned within cavity 22. In some examples, the length of cavity 22 measured along longitudinal axis 13 (e.g., the distance between first and second balloons 18 and 20) may be about 5 mm to about 40 mm.

When both first and second balloons 18 and 20 are inflated to the respective expanded states and engage with vessel 30, first and second balloons 18 and 20 form cavity 22. In some examples, cavity 22 may be a region created by the wall of vessel 30, the exterior surfaces of first and second balloons 18 and 20 when first and second balloons 18 and 20 are inflated in vessel 30, and any region (if any) of elongated member 12 separating first and second balloons 18 and 20. Fluid 36 may be contained within cavity 22 by the vessel wall 36 and the exterior surfaces of first and second balloons 18 and 20 such that fluid 36 lies in direct contact with vessel wall 36. In some examples, cavity 22 may define a tubular shape that encircles part of the exterior surface of distal portion 16B, limited by first and second balloons 18 and 20 and vessel wall 36.

Cavity 22 may be filled with a fluid 36 capable of undergoing cavitation via energy delivered to fluid 36 by electrode 24. In some examples, fluid 36 may be or include residual blood within vessel 30 confined within cavity 22 by first and second balloons 18 and 20. In addition to or instead of the residual blood, in some examples, fluid 36 may be or otherwise include a fluid introduced into cavity 22, such as, but not limited to, saline. In these examples, fluid 36 includes fluid not found in the patient's body, but, rather, introduced into cavity 22 by a clinician. In examples in which fluid 36 is introduced into cavity 22, fluid 36 may be introduced into cavity 22 using any suitable technique. In some examples, elongated member 12 may define one or more lumens 38 configured to provide access to cavity 22. Lumen 38 may permit the delivery of fluid 36, such as saline, into cavity 22 via one of supply tubes 26 and access ports 40 defined by elongated member 12.

In some examples, lumen 38 and access ports 40 may be used to perfuse cavity 22 with fluid 36 during the cavitation procedure. The perfusion of fluid 36 may help resupply fluid to cavity 22 that is lost due to leakage across one or more of first and second balloons 18 and 20. Additionally, or alternatively, the perfusion of fluid 36 into cavity 22 during the cavitation procedure may help dissipate heat within cavity 22 generated during the cavitation process.

Any suitable fluid 36 may be introduced into cavity 22 for the cavitation procedure. Example fluids 36 may include, but are not limited to, biocompatible fluids such as saline, phosphate buffered saline (PBS), or similar solution with a salt content between about 0.9 weight percent (wt. %) and about 5 wt. %; contrast media (e.g., about 25 volume percent (vol. %) to about 75 vol. % contrast media), or the like. Saline or other ionic solutions may more readily undergo cavitation compared to blood, thereby requiring less energy to induce cavitation within fluid 36 in cavity 22. For example, the higher the salt content of the saline fluid, the higher the conductance will be for the fluid, thereby requiring less energy to increase the temperature of the fluid and induce cavitation. Additionally, the higher the concentration of contrast media, the more viscous fluid 36 will be leading to a higher dissipation of the cavitation bubbles. In some examples, fluid 36 may be heated (e.g., body temperature or about 37° C.) prior to introduction into cavity 22. Heating fluid 36 may increase the relative vapor pressure of the fluid and thus require less energy to induce cavitation.

In some such examples, lumen 38 and access port 40 may also be configured to aspirate cavity 22 to remove blood, fluid 36 (e.g., pre- or post-cavitation), or other materials as part of the cavitation procedure. For example, a vacuum source may be connected to one of supply tubes 26 to cause a fluid within cavity 22 to be suctioned from the cavity via lumen 38 and access port 40. Additionally, or alternatively, elongated member 12 may define a different lumen (e.g., a lumen other than lumen 38 of FIG. 2) with access to cavity 22 for purposes of aspirating cavity 22, or catheter 10 may be used in conjunction with an aspiration catheter.

In some examples, cavity 22 may be perfused with fluid 36 and aspirated multiple times during the cavitation procedure to remove any unwanted material from cavity 22. For example, catheter 10 may include a dedicated lumen to supply fluid 36 to cavity 22 and a separate lumen dedicated to aspirating cavity 22. During the cavitation procedure, cavity 22 may be filled with fluid 36 and cavitated via energy delivered by electrode 24, then fluid 36 (along with any debris of calcified lesion 34) may be removed from cavity 22 via aspiration and fresh fluid 36 supplied to cavity 22. The entire procedure may then be repeated until calcified lesion 34 has been sufficiently treated.

Distal portion 16B of catheter 10 also includes at least one electrode 24 configured to deliver energy to fluid 36 within cavity 22 to cause fluid 36 to undergo cavitation. The term electrode may refer to the component(s) or portions of the component(s) that are used to induce cavitation within cavity 22 and is not intended to imply that the entire cavitation system is included in cavity 22. For example, while electrode 24 may refer to one or more portions of a conductor(s), marker band(s), or the like positioned in cavity 22, it is understood that the energy source for such componentry may not be located within cavity 22 and may be exterior to the body of a patient.

During the cavitation procedure, energy in the form of, for example, an electrical signal (e.g., electrical pulse) may be delivered to fluid 36 via electrode 24 to heat a portion of fluid 36 to generate a steam/plasma bubbles within fluid 36. The steam/plasma bubbles may represent relatively low-pressure pockets of vapor generated from the surrounding fluid 36. The low-pressure steam/plasma bubbles eventually collapse in on themselves due to the relatively high pressure of the surrounding fluid 36 and heat loss of the steam/plasma bubbles to the surrounding fluid 36. As the steam/plasma bubbles collapse, the bubbles release a large amount of energy in the form of a high-energy pressure pulse wave within fluid 36. In some examples, the formation and subsequent collapse of the steam/plasma bubbles may be short lived or nearly instantaneous, causing the pressure pulse waves to originate near the source of energy delivered to fluid 36 by electrode 24.

The pressure pulse waves may propagate through fluid 36 where they impact the wall of vessel 30 transmitting the mechanical energy of the pressure pulse wave into the tissue of vessel 30 and calcified lesion 34 on or within the vessel wall. The energy transmitted to calcified lesion 34 may cause the lesion to fracture or break apart allowing vessel 30 to be subsequently expanded (e.g., via first or second balloon 18 or 20 or a different expansion balloon using balloon angioplasty (e.g., plain old balloon angioplasty or POBA)) to a larger flow diameter.

By conducting the cavitation procedure in vessel 30 within fluid 36 in direct and intimate contact with the wall of vessel 30, the transfer of energy from the pressure pulse waves to calcified lesion 34 may be more efficient as compared to a cavitation procedure that introduces one or more intermediate devices, such as a sidewall of a balloon that may otherwise dampen the pulse energy, between the source of cavitation (e.g., electrode 24) and calcified lesion 34. In some examples, the improved efficiency of the process may require less energy to be transmitted to fluid 36 to incur the same amount of cavitation forces. Further, as the temperature of fluid 36 will increase as a consequence of the cavitation procedure, reducing the overall energy delivered to fluid 36 may also help reduce the temperature increase to fluid 36 caused by the delivery of energy to fluid 36. The more efficient transfer of energy from the pressure pulse waves to calcified lesion 34 may also reduce the duration that the cavitation procedure must be performed in order to sufficiently fracture or break apart calcified lesion 34 resulting in an overall shorter procedure. In some examples, by cavitating fluid 36 within cavity 22, the space provided by cavity 22 may allow for the resultant plasma bubbles to grow before collapsing which may help increase the resultant pressure created by the pressure pulse waves.

Additionally, or alternatively, due to the improved efficiency of the cavitation process, the profile of catheter 10 may be reduced. For example, the lower power requirements may mean that the components powering electrode 24 (e.g., the conductors supplying electrode 24) may require a lower energy load thereby allowing for smaller gauge of components to be incorporated into catheter 10. In some examples, the lowered power demands may also permit catheter 10 and the associated energy source to be operated as a handheld unit.

Figure 3A:
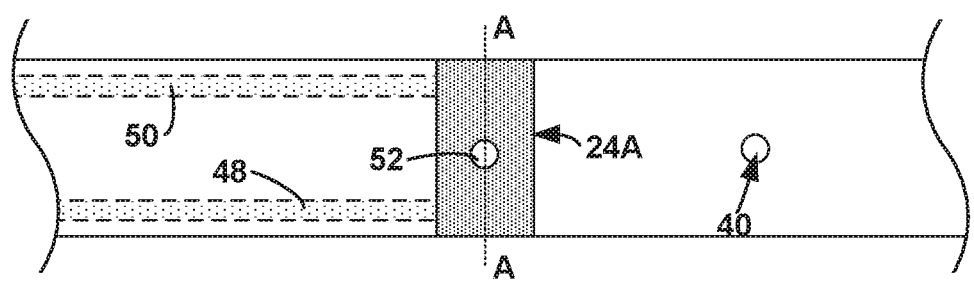
FIGS. 3A and 3B are schematic side views of an example concentric electrode that may be used with the catheter of FIG. 1.
Figure 3B:
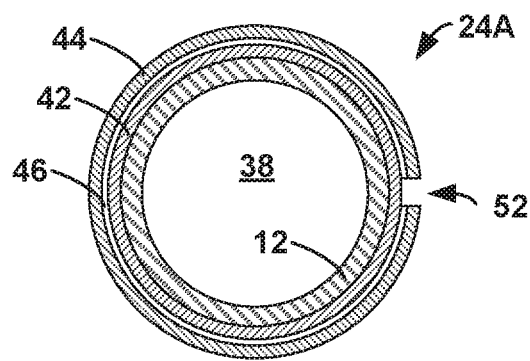

Electrode 24 may include any suitable device configured to deliver energy to fluid 36 within cavity 22 to cause fluid 36 to undergo cavitation. In some examples, electrode 24 may include both a supply or positive terminus and return or negative terminus to allow for the delivery of electrical energy through fluid 36 to induce cavitation. For example, as shown in the example of FIG. 2, electrode 24 may include a concentric electrode. FIGS. 3A and 3B are schematic side views of an example concentric electrode 24A that may be used with catheter 10. FIG. 3A illustrates an example side view of concentric electrode 24A and FIG. 3B illustrates an example cross sectional view of concentric electrode 24A taken through line A-A of FIG. 3A.

Concentric electrode 24A may include an inner and outer conductive band 42 and 44 respectively separated by an electrically insulative layer 46 (e.g., fluorinated ethylene propylene (FEP)). Inner and outer conductive bands 42 and 44 may each be electrically coupled to a respective electrical conductor 48 and 50 extending along elongated member 12. An electrode aperture 52 may pass through outer conductive band 44 and electrically insulative layer 46 to provide fluid communication between inner and outer conductive bands 42 and 44 (e.g., via fluid 36). That is, outer conductive band 44 and electrically insulative layer 46 may together define electrode aperture 52. Conductive bands 42 and 44 may have any suitable length to permit coupling to electrical conductors 48 and 50. In some examples, each conductive band 42 and 44 may comprise a ring or cylindrical body that defines a longitudinal length of about 1 mm. In some examples, conductive bands 42 and 44 may be formed from a marker band, hypotube, or other suitable device.

During a cavitation procedure, an electrical signal (e.g., an electrical pulse) may be delivered between inner and outer conductive bands 42 and 44 using fluid 36 captured within electrode aperture 52 to induce cavitation of fluid 36. The electrical signal transmitted may form a corona, an electrical arc, a spark, or the like between the pair of inner and outer conductive bands 42 and 44 using fluid 36 as the conductive media. In some examples, outer conductive band 44 may represent the return electrode such that the current density along the exposed surface area of inner conductive band 42 is maximized. Additionally, or alternatively, the exposed surface areas of inner conductive band 42 and outer conductive band 44 may be relatively small to maximize the current density. In some examples, the size or material of respective electrical conductors 48 and 50 may selected to accommodate the desired current density inner and outer conductive bands 42 and 44.

Electrode aperture 52 may take on any suitable shape and size. In some examples, the size and shape of electrode aperture 52 may guide the direction or size of the acoustic output of the pressure pulse waves. In some examples, electrode apertures 52 of neighboring electrodes 24 may be oriented in different circumferential directions along elongated member 12. Cavitation generated at the exposed surfaces of the electrode apertures 52 may then produce pressure pulse waves directed in different circumferential directions within vessel 30. In some examples, electrode aperture 52 may be in the shape of a ring around elongated member 12.

The electrical signal transmitted and received between inner and outer conductive bands 42 and 44 may be delivered from an energy source separate from catheter 10 (e.g., energy source 70 of FIG. 7) using electrical conductors 48 and 50. Electrical conductors 48 and 50 may extend from proximal portion 16A of catheter 10 to electrode 24A. A proximal end of electrical conductors 48 and 50 may be electrically connected to the external energy source in order to electrically connect electrode 24A to the energy source. For example, the proximal end of conductors 48 and 50 may extend through one or more of supply tubes 26 or may be connected to electrical contacts at or near proximal end 16A of catheter 10. The electrical contacts may then be directly electrically connected to the energy source or electrically connected to the energy source via a lead or another suitable electrical conductor.

While only a single electrode 24, 24A is illustrated in FIGS. 2 and 3B, catheter 10 may include a plurality of electrodes 24 each exposed to fluid 36 within cavity 22. In some examples, the number of electrodes 24 included on catheter 10 may depend on the size and shape of calcified lesion 34. For example, for longer lesions 34, more electrodes 24 may be used to induce cavitation of fluid 36 along the entire length the lesion 34 without needing to reposition catheter 10 during the procedure. In examples where concentric electrodes 24A are incorporated, each concentric electrode 24A may be separated by a distance of about 2 mm to 5 mm along longitudinal axis 13 to prevent shorting between neighboring electrodes.

Figure 4:
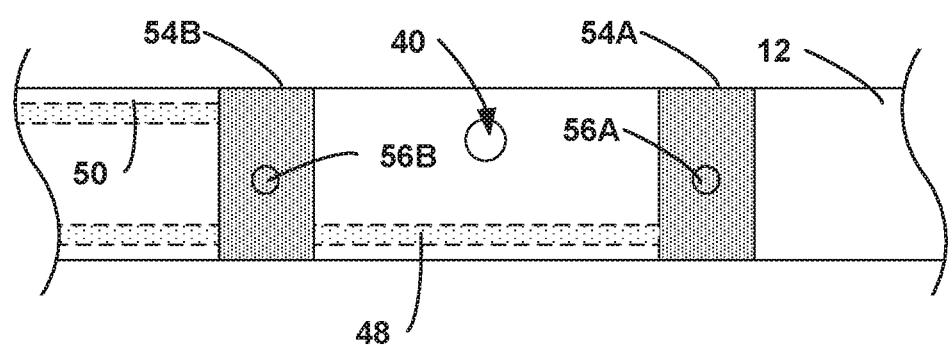
FIGS. 4-6 illustrate additional examples of electrode configurations that may be incorporated as the electrode of the catheter of FIG. 1.
Figure 5:
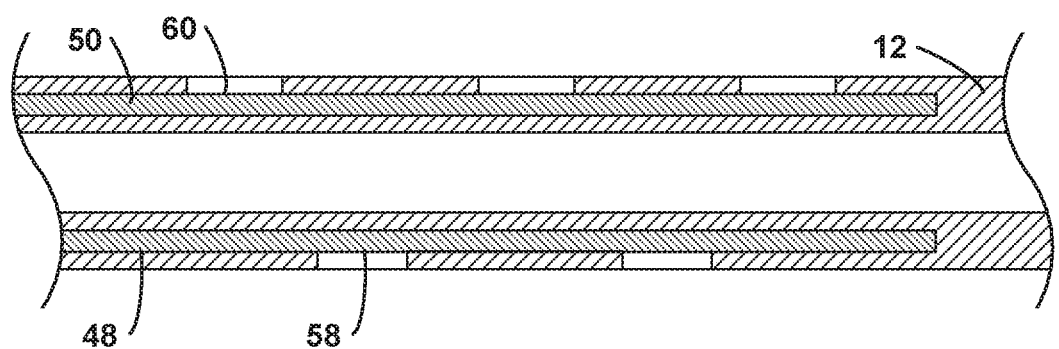
Figure 6:
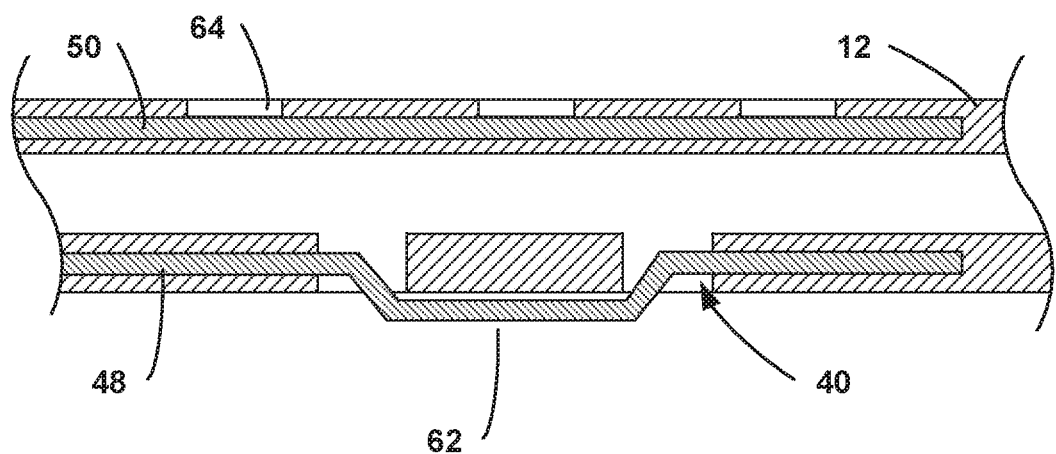

FIGS. 4-6 illustrate additional examples of electrode configurations that may be incorporated as electrode 24 of catheter 10. FIG. 4 is a side view of a pair of conductive bands 54A and 54B (collectively "conductive bands 54") at different longitudinal positions along elongated member 12. Conductive bands 54 may be powered by electrical conductors 48 and 50 respectively. In such examples, the catheter may be considered to include at least two electrodes 24 (e.g., conductive bands 54A and 54B). While only two conductive bands 54 are shown in FIG. 4, catheter 10 may include any suitable number of conductive bands 54 spaced along the length of elongated member 12. Each conductive band 54A and 54B may include at least one exposed surface 56A and 56B to fluid 36 within cavity 22 that is electrically conductive.

In some examples, conductive bands 54 may include at least one conductive band (e.g., conductive band 54A) operating as a supply or positive electrode and another conductive band (e.g., conductive band 54B) operating as a return or negative electrode. In such examples, the electrical signal delivered by the energy source may be delivered between the conductive bands 54A and 54B as an arc or corona using fluid 36 as the conductive medium. The separation distance between conductive bands 54A and 54B along a longitudinal axis 13 may determine whether the electrical signal is delivered as an arc or corona. In examples in which an arc discharge is desired, exposed surfaces 56A and 56B of conductive bands 54A and 54B may be separated by less than about 0.5 mm. In examples in which a corona discharge is desired, exposed surfaces 56A and 56B of conductive bands 54A and 54B may be separated by the same distance (e.g., less than about 0.5 mm) or a much greater distance (e.g., separated by a distance of about 1 mm to about 5 mm). The total number of conductive bands 54 may be chosen depending on the size of lesion 34 at the target treatment site and the type of electrical signal delivery desired.

Each conductive band 54A and 54B may include at least one exposed surface 56A and 56B to fluid 36 within cavity 22 that provides a location for where the cavitation can occur. In some examples, an outer jacket may be heat shrunk over conductive bands 54A and 54B with a portion of the outer jacket being removed (e.g., laser or mechanically etched or otherwise cut) to form each of exposed surfaces 56A and 56B. Each exposed surface 56A and 56B may define a respective electrode within cavity 22. An electrical signal can be delivered between the exposed surfaces 56A and 56B of conductive bands 54A and 54B by treating one as a source electrode (e.g., positive terminus) and the other as the return electrode (e.g., negative terminus) to induce cavitation of fluid 36. The site for cavitation may be controlled by controlling the surface area and/or materials of exposed surfaces 56A and 56B. The electrode with the smaller surface area may have a higher current density and therefore act as the site for cavitation to occur. Additionally, or alternatively, the direction of the resultant pressure pulse waves produced by the cavitation may be controlled based on the circumferential location of exposed surfaces 56A and 56B along elongated member 12. In some examples, exposed surfaces 56A and 56B may be oriented in different circumferential directions alone elongated member 12 to allow for 360° deployment of the pressure pulse waves within vessel 30. Additionally, or alternatively, the positioning of exposed surfaces 56A and 56B at different circumferential orientations along elongated member 12 may allow for the electrical signal transmitted between the electrodes to "walk" circumferentially around elongated member 12.

In some examples, elongated member 12 may include a plurality of conductive bands 54 electrically coupled to electrical conductors 48 and 50 in an alternating fashion or supplied by their own independent electrical conductor. Such configurations may allow for the electrical signal to be passed between adjacent pairs of conductive bands 54 using electrical conductors 48 and 50 or between selected conductive bands 54 respectively to induce cavitation at desired locations within cavity 22.

FIG. 5 is a cross-sectional view of another example electrode configuration, which is an example of electrode 24 (FIG. 1) that may be used with catheter 10. In the example electrode configuration of FIG. 5, electrical conductors 48 and 50 extend along elongated body 12 with at least one portion of each conductor 48 and 50 being exposed (e.g., expose surfaces 58 and 60 respectively) to fluid 36 within cavity 22. For example, electrical conductors 48 and 50 may represent electrical wires extending within the body (e.g., imbedded or within an inner lumen) of elongated member 12. The wires may be braided, coiled, or linearly extending along elongated member 12. In some examples, the wires may contribute or form part of the support structure of elongated member 12. Electrical conductors 48 and 50 may be electrically insulated from one another by an insulating sheath or by the body of elongated member 12 which may be comprised of non-conductive material (e.g., FEP). Each electrical conductors 48 and 50 may define at least one exposed surface 58 and 60 that allows electrical conductors 48 and 50 to be in direct contact with fluid 36. Exposed surfaces 58 and 60 of electrical conductors 48 and 50 may be formed by removing parts of elongated member 12 (e.g., laser etching) to expose electrically conductive surfaces 58 and 60 of conductors 48 and 50, respectively. Each exposed surface 58 and 60 may act as a respective electrode within cavity 22. During a cavitation procedure, an electrical signal can be delivered between one or more of the exposed surfaces 58 and 60 of conductors 48 and 50 to induce cavitation of fluid 36 in contact with both surfaces 58 and 60.

FIG. 6 is a cross-sectional view of another example electrode configuration that may be used with catheter 10. Similar to the electrode configuration of FIG. 5, electrical conductors 48 and 50 extend along elongated body 12 with at least one portion of each conductor 48 and 50 being exposed (e.g., exposed surfaces 62 and 64 respectively) to fluid 36 within cavity 22. In some examples, the exposed surface 62, 64 of one or both of conductors 48 and 50 may be formed by passing the respective conductor (e.g., conductor 48 in FIG. 6) along an exterior of elongated member 12. In such examples, the portion of the respective conductor extending along the exterior of elongated member 12 (e.g., exposed surface 62 of conductor 48 in FIG. 6) may be exposed to fluid 36 within cavity 22. Each exposed surface 62 and 64 may be characterized as an electrode within cavity 22. During the cavitation procedure, an electrical signal can be delivered between one or more of the exposed surfaces 62 and 64 of conductors 48 and 50 to induce cavitation of fluid 36 in contact with both surfaces 62 and 64.

In any of the above electrode configurations one or more access ports 40 may be used to introduce fluid 36 into cavity 22. In some examples, one or more of conductors 48 and 50 may share a common lumen that supplies fluid 36 to cavity 22. In some such examples, one or more of the access ports 40 permitting entrance of fluid 36 into cavity 22 may also be the location where electrical conductor 48 and/or 50 is also exposed to fluid 36 in the cavity.

Components of electrode 24 and including, for example, conductors 48 and 50 and/or conductive bands 44, 46, and 54 may be formed using any suitable electrically conductive material including, for example, titanium alloys (e.g., Ti—Mo alloy), platinum or platinum-iridium alloys, stainless steel, copper, copper alloys (e.g., copper and hafnium or tungsten), tungsten, or the like. In some examples, conductors 48 and 50 and conductive bands 44, 46, and 54 (where used) may be formed of the same material, while in other examples the components may be formed of different materials. In some examples, conductors 48 and 50 may be formed using metal wires extending along longitudinal axis 13 of elongated member 12. Portions of the metal wires may be exposed to fluid 36 via etching or other mechanism. In other examples, conductive bands 44, 46, and 54 may be formed separate from conductors 48 and 50 and electrically and mechanically connected to conductors 48 and 50.

In some examples, elongated member 12 may define a guidewire lumen (e.g., lumen 38) configured to receive a guidewire (not shown) used to help navigate distal portion 16B to target treatment site 32. For example, the guidewire may be introduced through vasculature of a patient to target treatment site 32 and distal portion 16B of catheter 10 may be advanced over the guidewire to navigate elongated member 12 through the vasculature of the patient to target treatment site 32.

In some examples, the intensity of the pressure pulse waves may be adjusted by controlling the intensity of the electrical signal delivered via electrodes 24, the separation distance between electrodes 24, the exposed surface area of the respective electrode 24, and the like. The intensity of the electrical signal may be function of one or more of a voltage, a current, a frequency (e.g., a pulse rate in the case of pulses), a pulse width, or one or more other electrical signal parameters.

In other examples, one of the electrodes associated with the cavitation procedure (e.g., the reference electrode) may be external to the patient. For example, catheter 10 may include electrode 24 positioned within vessel 30 of the patient and the reference or return electrode may be positioned on the external skin surface of the patient, e.g., as a pad electrode. The electrical signal may be delivered between the electrodes, through fluid 36 and the tissue of the patient to induce cavitation of fluid 36 at electrode 24.

Figure 7:
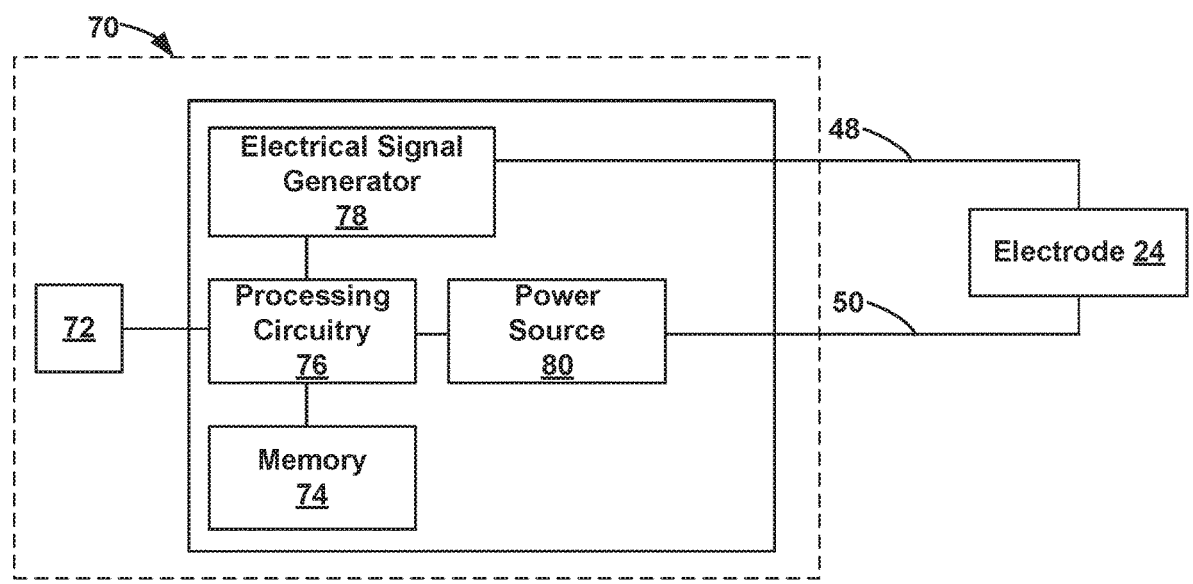
FIG. 7 is a schematic block diagram of an example cavitation energy source that may be used with the catheter of FIG. 1 to induce cavitation of within a fluid.

FIG. 7 shows a schematic block diagram of an example energy source 70 that may be used with catheter 10 to induce cavitation within fluid 36. Energy source 70 includes control mechanism 72, memory 74, processing circuitry 76, electrical signal generator 78, and power source 80.

Processing circuitry 76 may include any one or more microprocessors, controllers, digital signal processors (DSPs), application specific integrated circuits (ASICs), field-programmable gate arrays (FPGAs), discrete logic circuitry, or any processing circuitry configured to perform the features attributed to processing circuitry 76. The functions attributed to processors described herein, including processing circuitry 76, may be provided by a hardware device and embodied as software, firmware, hardware, or any combination thereof. In some examples, processing circuity 76 may include instructions to recognize a particular electrode 24 configuration or allow a clinician to manually input the specific electrode 24 configuration of catheter 10. In some examples, energy source 70 may include additional components such as, a display device or user input device that are not expressly shown for displaying information from processing circuitry 76 or allowing the clinician to input information.

Memory 74 may include any volatile or non-volatile media, such as a random access memory (RAM), read only memory (ROM), non-volatile RAM (NVRAM), electrically erasable programmable ROM (EEPROM), flash memory, and the like. Memory 74 may store computer-readable instructions that, when executed by processing circuitry 76, cause processing circuitry 76 to perform various functions described herein. Memory 74 may be considered, in some examples, a non-transitory computer-readable storage medium including instructions that cause one or more processors, such as, e.g., processing circuitry 76, to implement one or more of the example techniques described in this disclosure. The term "non-transitory" may indicate that the storage medium is not embodied in a carrier wave or a propagated signal. However, the term "non-transitory" should not be interpreted to mean that memory 74 is non-movable. As one example, memory 74 may be removed from energy source 70, and moved to another device. In certain examples, a non-transitory storage medium may store data that can, over time, change (e.g., in RAM).

Processing circuitry 76 is configured to control energy source 70 and electrical signal generator 78 to generate and deliver the electrical signal across one or more electrodes 24 to induce cavitation of fluid 36. Electrical signal generator 78 includes electrical signal generation circuitry and is configured to generate and deliver an electrical signal in the form of pulses and/or a continuous wave electrical signal. In the case of electrical pulses, electrical signal generator 78 may be configured to generate and deliver pulses having an amplitude of about 500 volts (V) to about 5000 V (e.g., between about 1500 V to about 3000 V), a pulse width of about 1 microsecond (μs) to about 5 μs for arc-type cavitation or about 10 μs to about 200 μs for corona-type cavitation, and a frequency of about 0.5 Hertz (Hz) to about 1000 Hz. In some examples, catheter 10 may be configured such that conductors 48 and 50 are independently coupled to one or more electrodes 24. In such examples, processing circuitry 76 may control electrical signal generator 78 to generate and deliver multiple electrical signals via different combinations of conductors 48 and 50 and/or electrodes 24. In these examples, energy source 70 may include a switching circuitry to switch the delivery of the electrical signal using electrodes 24, e.g., in response to control by processing circuitry 76.

Power source 80 delivers operating power to various components of energy source 70. In some examples, power source 80 may represent hard-wired electrical supply of alternating or direct electrical current. In other examples, power source 80 may include a small rechargeable or non-rechargeable battery and a power generation circuit to produce the operating power. Recharging may be accomplished through proximal inductive interaction between an external charger and an inductive charging coil within energy source 70.

A control mechanism 72, such as foot pedal, handheld, or remote-control device, may be connected to energy source 70 to allow the clinician to initiate, terminate and, optionally, adjust various operational characteristics of energy source 70, including, but not limited to, power delivery. Control mechanism 72 can be positioned in a sterile field and operably coupled to the energy source 70 and can be configured to allow the clinician to selectively activate and deactivate the energy delivered to one or more electrode 24. In other embodiments, control mechanism 72 may be built into hub 14.

Figure 8:
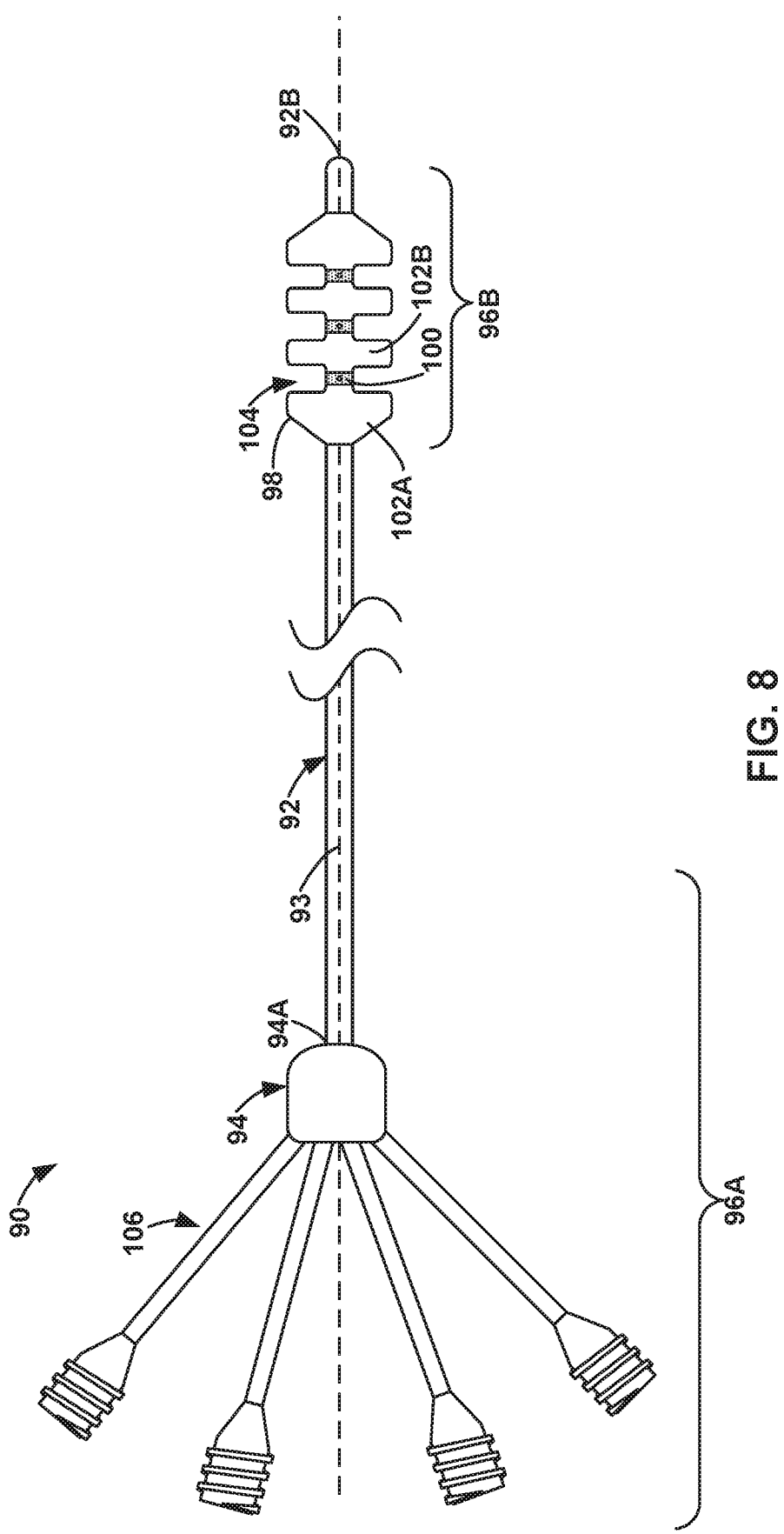
FIG. 8 is a schematic side view of another example catheter, the side view showing the catheter along a longitudinal axis of the elongated member.

In some examples, cavity 22 may be formed using a single balloon with one or more electrodes positioned over the balloon configured to restrict the inflation of the balloon, thereby forming the respective cavities. FIG. 8 is a schematic side view of another example catheter 90, which includes an elongated member 92 extending from proximal end 92A to distal end 92B. The side view of FIG. 8 is shown along a longitudinal axis 93 of elongated member 92.

Catheter 90 includes a hub 94 connected to proximal end 92A of elongated member 92. Hub 94, including proximal end 92A of elongated member 92, forms part of a proximal portion 96A of catheter 90. Catheter 90 also includes a distal portion 96B that includes distal end 92B of elongated member 92. The various components of catheter 90 including, for example, hub 94, supply tubes 106, elongated member 92, and the like may be substantially similar to the components of catheter 10 described above apart from any differences described below.

Figure 9:
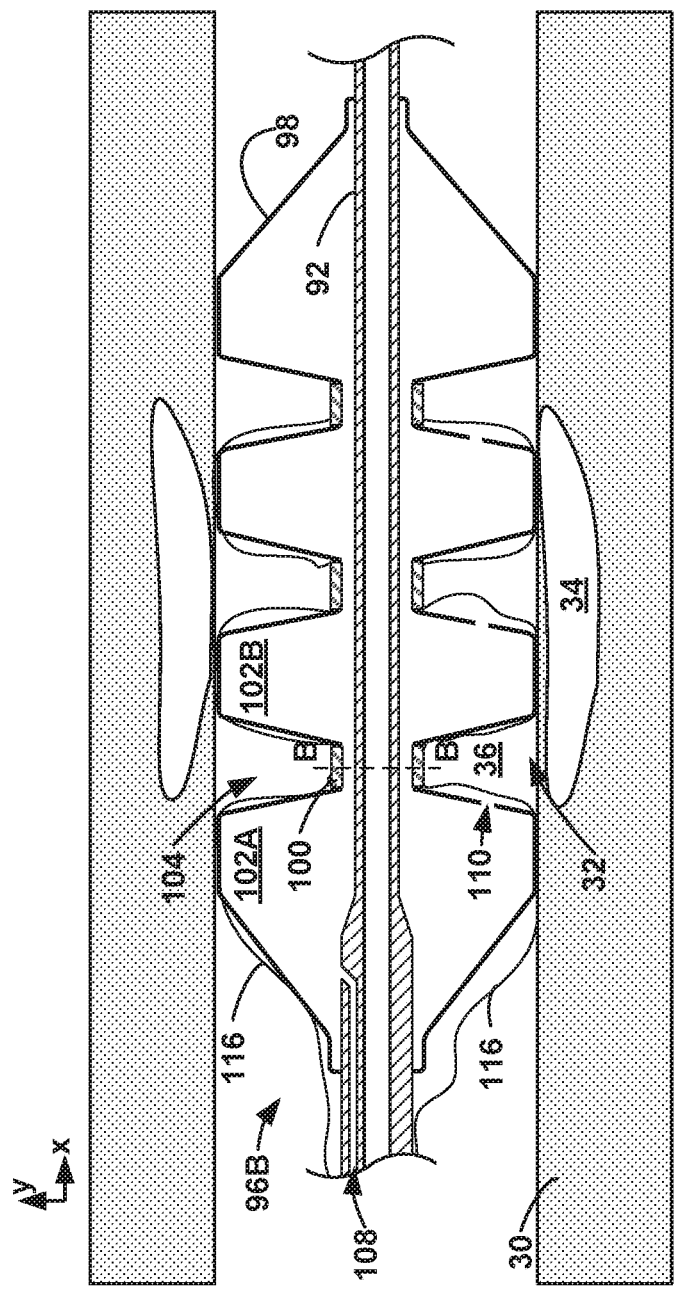
FIG. 9 is an enlarged conceptual cross-sectional view of a distal portion of the catheter of FIG. 8 taken the along longitudinal axis of the elongated member.

FIG. 9 is an enlarged conceptual cross-sectional view of distal portion 96B of catheter 90 of FIG. 8, the side view illustrating distal portion 96B along longitudinal axis 93 of elongated member 92. FIG. 9 shows distal portion 96B deployed within vessel 30 of a patient, vessel 30 including a target treatment site 32 containing a calcified lesion 34 on or within a wall of vessel 30.

As shown in FIG. 9, distal portion 96B of catheter 90 includes a balloon 98 mechanically connected to elongated member 92 and configured to be inflated to an expanded state to occlude vessel 30 within the vasculature of a patient. Distal portion 96B also includes at least one electrode 100 carried by elongated member 92 and positioned over balloon 98. Each electrode 100 is configured to restrict the expansion of balloon 98 to cause balloon 98 to form a pair of balloon lobes (e.g., first lobe 102A and second lobe 102B, referred to collectively as "balloon lobes 102") when balloon 98 is inflated to the expanded state. Each pair of balloon lobes (e.g., first lobe 102A and second lobe 102B) define a cavity 104, which is a closed cavity when the respective pair of balloon lobes 102 contact a wall of the vessel 30 in the expanded state. Each respective electrode 100 has at least one surface exposed to fluid 36 received within cavity 104 formed by the respective pair of balloon lobes 102. The configuration of balloon 98 and electrode 100 may help center electrode 100 within vessel 30, which may help ensure a more equal distribution of the pressure pulse wave against the wall of vessel 30 during the cavitation process as well as reduce the chance of localized heating along the wall of vessel 30 by electrode 100.

Catheter 90 may include any suitable number of balloon lobes 102 and electrodes 100. In some examples, the total number of balloon lobes 102 and electrodes may depend on the size and length of lesion 34 to be treated. Balloon lobes 102 and electrodes 100 may be any suitable size and length. In some examples, each electrode 100 may define a length along longitudinal axis 93 of about 1 mm and each lobe 102 may define a length along longitudinal axis 93 of about 3 mm to about 4 mm, however, other lengths may also be used. In some examples, the length of electrode 100 may be adjusted to increase or decrease the resultant size of respective cavities 104.

Figure 10:
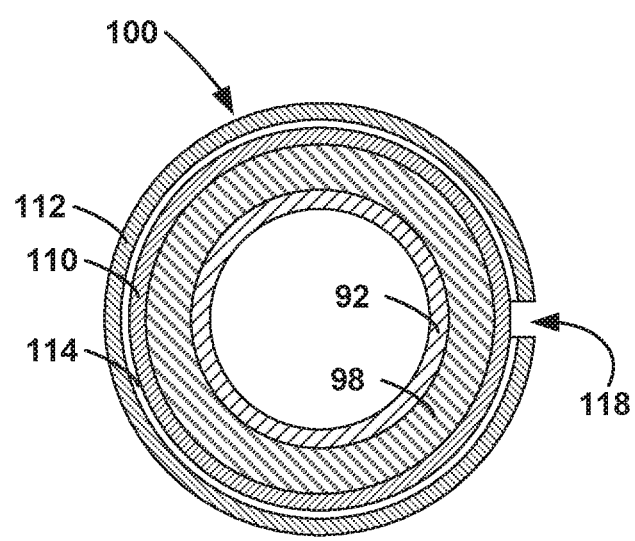
FIG. 10 is an example side view of the electrode of FIG. 9 taken through line B-B.

FIG. 10 is an example side view of electrode 100 taken through line B-B of FIG. 9. In some examples, electrode 100 may include a concentric electrode (e.g., similar to concentric electrode 24A described above with respect to FIGS. 3A and 3B) positioned over balloon 98 to partially restrict the inflation of balloon 98. While electrode 100 is primarily shown and described as being a concentric electrode, other electrode configurations (e.g., those shown and described in FIGS. 4-6) may also be used.

Electrode 100 may include an inner and outer conductive band 110 and 112 respectively separated by an electrically insulative layer 114. Inner and outer conductive bands 110 and 112 may each be electrically coupled to a respective electrical conductor (e.g., electrical conductors 116) that extends along elongated member 92. Electrode 100 may define an electrode aperture 118 of any suitable size and shape (e.g., hole or ring) that passes through outer conductive band 112 and electrically insulative layer 114 to provide fluid communication between inner and outer conductive bands 110 and 112 (e.g., via fluid 36). Conductive bands 110 and 112 may have any suitable length. In some examples, each conductive band 110 and 112 may comprise a ring or cylindrical body that defines a longitudinal length of about 1 mm. In some such examples, balloon 98 may define a length of about 25 mm to about 100 mm, but length of balloon 98 may be increased or decreased depending on the total number of electrodes 100 and length of target treatment site 32.

During the cavitation procedure, an electrical signal may be delivered between inner and outer conductive bands 110 and 112 using fluid 36 captured within electrode aperture 118. The electrical signal transmitted may form a corona, an electrical arc, a spark, or the like between the pair inner and outer conductive bands 110 and 112 using fluid 36 as a conductive media to cause fluid 36 to undergo cavitation. The electrical signal transmitted and received between inner and outer conductive bands 110 and 112 may be delivered to electrode 100 from an energy source (e.g., energy source 70) using electrical conductors 116.

As described further below, in some examples, electrical conductors 116 may extend from proximal portion 96A of catheter 90 to electrode 100. Electrical conductors 116 may pass either external to balloon 98 as illustrated in FIG. 9 or pass through an interior portion of balloon 98, such as through a sidewall of the balloon or through relatively small holes in balloon 98 to allow to electrically couple to one or more electrodes 100 to electrical conductors 116. The holes in balloon 98 may be occupied by the electrical conductor(s) 116, such that little to no inflation fluid escapes from balloon 98 when balloon 98 is inflated and balloon 98 is able to remain inflated at the desired pressure during a medical procedure. Additionally, or alternatively, balloon 98 may include an electrically conductive material embedded within the (electrically insulative) sidewall of the balloon (e.g., small gauge wire or a conducive polymer) to transmit the electrical signal between electrode 100 and electrical conductors 116, or between two or more electrodes 100.

A proximal portion of electrical conductors 116 (e.g., the portion of electrical conductors 116 proximal to balloon 98) may extend along the exterior of elongated member 92, secured to or within elongated member 92 (e.g., secured via a heat shrunk outer jacket), or may passed along an inner lumen of elongated member 92. In some examples, the proximal portion of electricals conductors 116 may be braided or coiled around elongated member 92 and subsequently unbraided or uncoiled as the electricals conductors 116 pass along balloon 98. A proximal end of electrical conductors 116 may be electrically connected to an energy source (e.g., energy source 70 of FIG. 7) in order to electrically connect electrode 100 to the energy source. In some examples where distal portion 96B includes a plurality of electrodes 100, each contained within a different cavities 104, each electrical conductor 116 may be coupled to a respective electrode 100 to provide independent activation to each electrode 100. In some such examples, at least one of electrical conductors 116 may serve as a common conductor (e.g., reference wire) for each electrode 100.

In the respective expanded state within vessel 30, the various balloon lobes 102 of balloon 98 inflate and conform to engage with the wall of vessel 30. In some examples, balloon 98 may be inflated via an inflation lumen 108 accessed by one of supply tubes 106 by the introduction of a saline or contrast solution. In some examples, one or more of balloon lobes 102 may include a perfusion port 110 that may be used to fill one or more of cavities 104 with fluid 36. Perfusion port 110 may be used to resupply fluid 36 or continuously supply fluid 36 to a respective cavity 104 during the cavitation process. In some examples, perfusion port 110 may be sized to introduce fluid 36 into cavity 104 at a flow rate of about 1 mL/min to about 10 mL/min, when balloon 98 is inflated to a pressure of about 2-6 atmospheres.

Balloon 98 may be formed from any suitable material, such as, but not limited to, a flexible polymeric material that forms a tight seal with elongated member 92. In some examples, balloon 98 may be configured to be deflatable via a vacuum or other stable source to forcibly remove fluid from the balloon (e.g., remove fluid at about 1 mL/min). Additionally, or alternatively, balloon 98 may be a wrapped balloon defining a plurality of pleats 112 that are configured to be wrapped around elongated member 92 while balloon 98 is in a collapsed state.

Figure 11A:
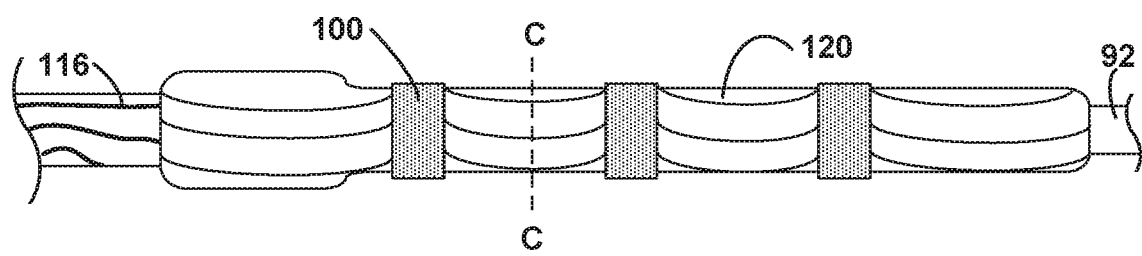
FIGS. 11A-11C are schematic views of an example wrapped balloon in a collapsed state, which may be used as the balloon on the catheter of FIG. 8.
Figure 11B:
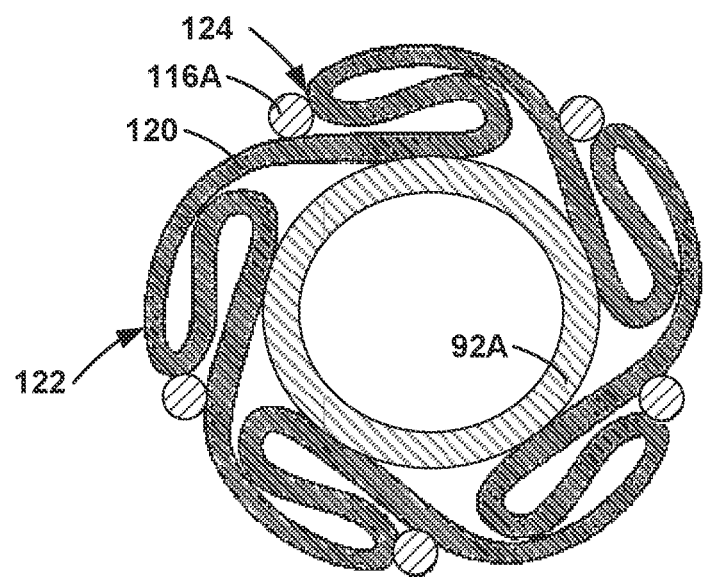
Figure 11C:
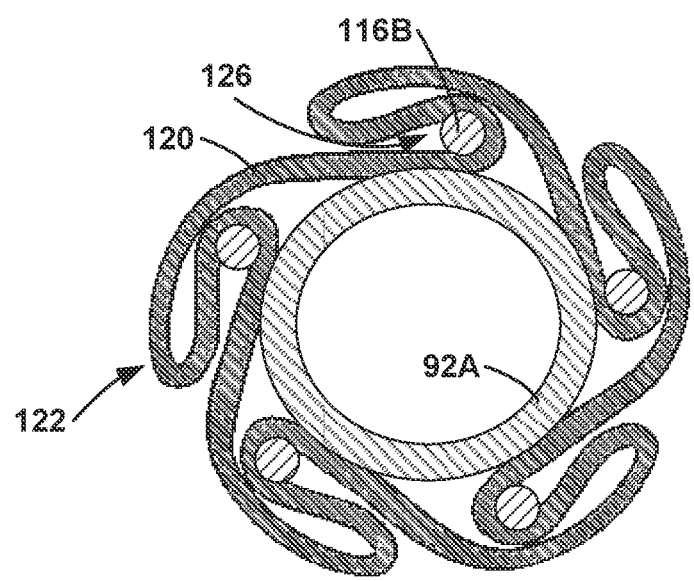

FIGS. 11A-11C are schematic views of an example wrapped balloon 120 in a collapsed (uninflated) state. FIG. 11A is a side view and FIGS. 11B and 11C are cross-sectional views of wrapped balloon 120 along cross section C-C of FIG. 11A showing different ways electrical conductors 116 may be incorporated along the exterior of wrapped balloon 120 while in the collapsed state. The cross-section is taken through one of respective balloon lobe areas (e.g., second lobe 102B) which does not include an electrode. Wrapped balloon 120 may be used as balloon 98.

As shown in FIGS. 11B and 11C, wrapped balloon 120 defines a plurality of pleats 122, which are wrapped (e.g., folded) around elongated member 92A. Each pleat 122 may be wrapped in the same direction such that pleats 122 may be laid on top of one another around the outer perimeter (e.g., a circumference if circular in cross-section) of elongated member 92A.

FIG. 11B and 11C illustrate different techniques for how electrical conductors 116A and 116B may be incorporated along the exterior of wrapped balloon 120 while the balloon is in a collapsed state. FIG. 11B shows that electrical conductors 116A can be positioned adjacent to the apex 124 of each pleat 122, while FIG. 11C shows electrical conductors 116B disposed within the inner folds 126 of each pleat 122. The configuration of electrical conductors 116A in FIG. 11B may allow the one or more electrodes (e.g., electrode 100) to be assembled over wrapped balloon 120 after balloon 120 has been attached and wrapped around elongated member 92A, while the configuration of electrical conductors 116B in FIG. 11C may help to at least partially protect electrical conductors 116B while wrapped balloon 120 is being navigated through the vasculature of the patient. In both cases, electrical conductors 116A and 116B may include sufficient slack to allow for the expansion of wrapped balloon 120 without being decoupled from the respective electrode.

Figure 12:
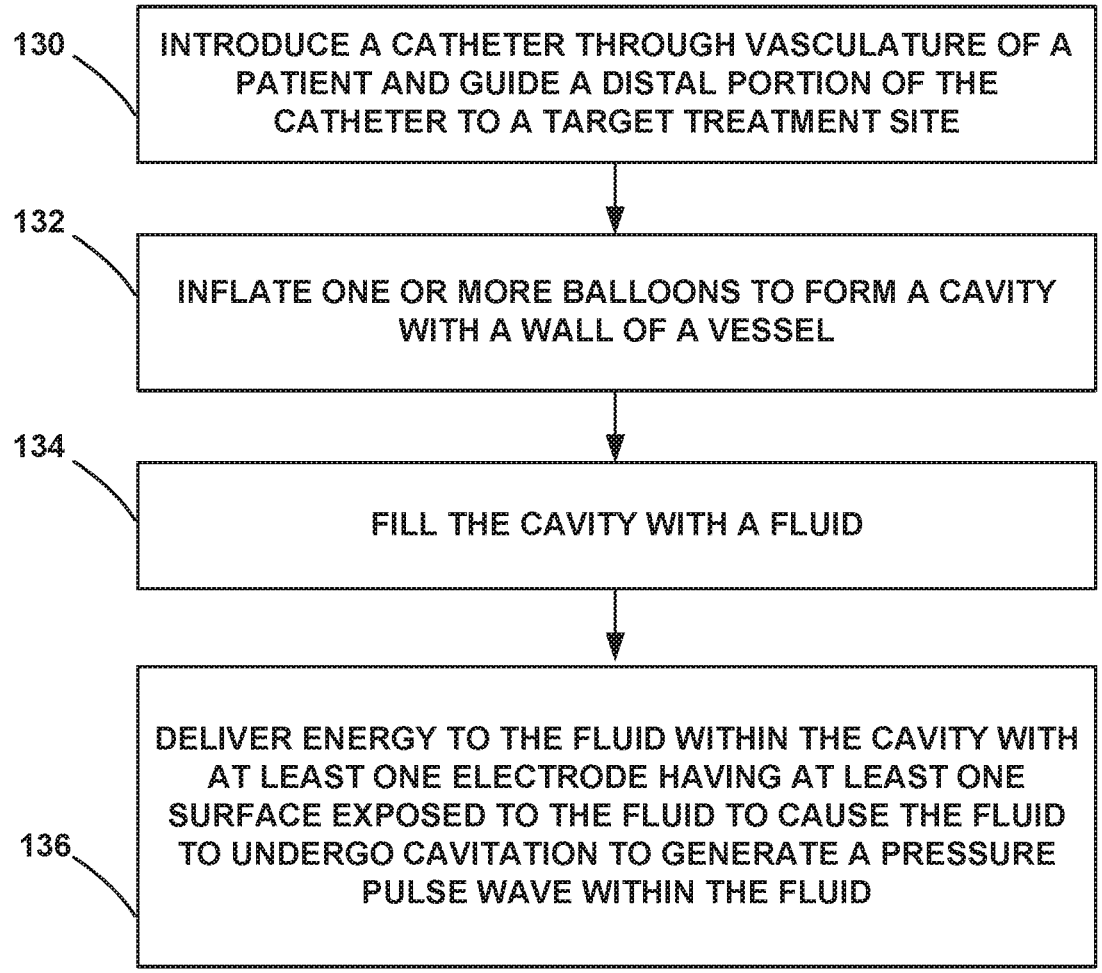
FIG. 12 is a flow diagram of an example technique of using the catheters described herein.

FIG. 12 is a flow diagram of an example technique of using catheters 10 or 90 described herein. For illustrative purposes, the techniques of FIG. 12 are described with reference to the various aspects of catheter 10 or 90, however, such descriptions are not intended to be limiting and the techniques of FIG. 12 may be used with other catheters or catheters 10 and 90 may be used in other applications.

The technique of FIG. 12 includes introducing a catheter 10 through vasculature of a patient and guide a distal portion 16B of catheter 10 to a target treatment site 32 adjacent to a calcified lesion 34 (130), inflating one or more balloons to a respective expanded state to form a cavity with the wall of vessel 30 (132). As described above, distal portion 16B may include a first and second balloons 18 and 20 connected to elongated member 12 and separated by a distance such that such when inflated to engage with vessel wall 36, first balloon 18 occludes a proximal portion of vessel 30 proximal to target treatment site 32 and second balloon 18 occludes a distal portion of vessel 30 distal to target treatment site 32 to form cavity 22 that is exterior to the first and second balloons 18 and 20. In other examples, the balloon may include a single balloon (e.g., balloon 98) with the balloon being inflated to form multiple balloon lobes 102 that form a cavity 104 between adjacent lobes 102.

In some examples, first and second balloons 18 and 20 may be independently expanded using different lumens to expand first and second balloons 18 and 20. In some such examples, first and second balloons 18 and 20 may be sequentially expanded in an order that follows the direction of blood flow within vessel 30. For example, if blood flows in the x-axis direction of FIG. 2, first balloon 18 may be inflated prior to inflating second balloon 20. In some examples, sequentially inflating first and second balloons 18 and 20 in such a manner may assist with removing blood from cavity 22 by allowing blood to continue to flow from cavity 22 prior to second balloon 20 being inflated.

During or after first and second balloons 18 and 20 have been inflated to engage vessel wall 36, cavity 22 may be filled with fluid 36 (134). In some examples, cavity 22 may be filled with fluid 36 using a lumen 38 and access port 40 defined by elongated member 12 configured to provide access to cavity 22. Fluid 36 may include any suitable fluid capable of undergoing a cavitation procedure. In some examples, cavity 22 may be aspirated (e.g., using lumen 38) prior to filling cavity 22 with fluid 36 and/or after the cavitation procedure to remove fluid 36 and other materials from cavity 22 before deflating first and second balloons 18 and 20.

The technique of FIG. 12 also includes delivering energy 48 to fluid 36 within cavity 22 using at least one electrode 24 having at least one surface exposed to fluid 36 (e.g., electrode 24 is positioned between the first and second balloons 18 and 20 within cavity 22) to cause fluid 36 to undergo cavitation to generate a pressure pulse wave within fluid 36 (136). As described above, electrode 24 may transmit energy to fluid 36 (e.g., electrical energy) that rapidly heats a portion of fluid 36 to produce short-lived gaseous steam/plasma bubbles within fluid 36. The steam/plasma bubbles may represent relatively low-pressure pockets of vapor generated from the surrounding fluid 36. The low-pressure steam/plasma bubbles eventually collapse in on themselves due to the relatively high pressure of the surrounding fluid 36. As steam/plasma bubbles collapse, the bubbles release a large amount of energy in the form of a high-energy pressure pulse wave within fluid 36 that propagate through fluid 36 where they impact the wall of vessel 30 transmitting the mechanical energy of the pressure pulse wave into the tissue of vessel 30 and calcified lesion 34. The energy transmitted to calcified lesion 34 may cause the lesion to fracture or beak apart. In some examples, this cavitation treatment of calcified lesion 34 may be used in conjunction with either first or second balloon 18 and 20 to help open-up vessel 30 of the patient, restoring the vasculature to a normal or larger flow diameter. Additionally, or alternatively, this cavitation treatment of calcified lesion 34 may be used in conjunction with POBA to restore the vasculature to a normal or larger flow diameter.

In some examples, the electrical energy delivered to fluid 36 via one or more electrodes 24 may be in the form of a corona, an electrical arc, a spark or the like. The electrical signal may be a continuous wave signal or in the form of a plurality of pulses, and may have any suitable electrical signal parameters for creating the cavitation. For example, the electrical signal may have an amplitude of about 500 volts (V) to about 5000 V, a pulse width of about 1 microsecond to about 200 microseconds, and a frequency of about 0.5 Hertz (Hz) to about 1000 Hz.

After the cavitation procedure using the technique of FIG. 12, first and second balloons 18 and 20 may be deflated and catheter 10 may be withdrawn from vessel 30.

Various examples have been described. These and other examples are within the scope of the following claims.

What is claimed is:
1. A catheter comprising:
an elongated member configured to be navigated through vasculature of a patient to a target treatment site;
a balloon connected to the elongated member, the balloon being inflatable to an expanded state to occlude a vessel of the patient; and
an electrode positioned around a portion of an exterior of the balloon, the electrode configured to electrically connect to an energy source configured to deliver an electrical signal, via the electrode, to a fluid in contact with the electrode to cause the fluid to undergo cavitation to generate a pressure pulse wave within the fluid, wherein, when the balloon is in the expanded state, the electrode is configured to cause the balloon to form a first lobe and a second lobe by restricting the expansion of the balloon, the first lobe and the second lobe being configured to form a cavity when the first lobe and the second lobe contact a wall of the vessel in the expanded state.

2. The catheter of claim 1, wherein the electrode comprises a concentric electrode comprising an outer electrically conductive band and an inner electrically conductive band separated by an electrically insulating layer, an aperture extending through the outer electrically conductive band and the electrically insulating layer to provide fluid communication between the outer and the inner electrically conductive bands.

3. The catheter of claim 1, wherein the electrode comprises a cylindrical body, the cylindrical body configured to maintain a cylindrical shape when the balloon is inflated to the expanded state.

4. The catheter of claim 1, wherein the electrode defines at least one surface exposed to the cavity.

5. The catheter of claim 1, wherein the balloon comprises a wrapped balloon comprising a plurality of pleats, wherein, when the balloon is in a non-expanded state, the pleats are wrapped around the elongated member.

6. The catheter of claim 5, further comprising an electrical conductor electrically coupled to the electrode, the electrical conductor extending along the elongated member and positioned along an exterior of the wrapped balloon.

7. The catheter of claim 6, wherein, when the balloon is in the non-expanded state, at least one pleat of the plurality of pleats is folded over the electrical conductor.

8. The catheter of claim 6, wherein, when the balloon is in the non-expanded state, the electrical conductor is positioned adjacent to an apex of at least one pleat of the plurality of pleats.

9. The catheter of claim 1, wherein the elongated member defines an inner lumen configured to receive a guidewire.

10. The catheter of claim 1, wherein the balloon defines at least one perfusion aperture configured to supply a fluid to the cavity.

11. The catheter of claim 1, wherein the balloon comprises at least one of an anti-restenotic agent, an anti-proliferative agent, or an anti-inflammatory agent.

12. The catheter of claim 1, wherein the electrode comprises a first electrode and the cavity comprises a first cavity, the catheter further comprising a second electrode positioned around a distal portion of the exterior of the balloon, wherein, when the balloon is in the expanded state, the second electrode is configured to cause the balloon to form a third lobe and the second lobe by restricting the expansion of the balloon, the second lobe and the third lobe configured to form a second cavity containing the second electrode when the second lobe and the third lobe contact the wall of the vessel in the expanded state.

* * * * *